(12) United States Patent
Cesarini et al.

(10) Patent No.: US 8,663,264 B2
(45) Date of Patent: *Mar. 4, 2014

(54) RECIPROCATING ROTARY ARTHROSCOPIC SURGICAL INSTRUMENT

(75) Inventors: Peter M. Cesarini, Londonderry, NH (US); Karen Drucker, Danville, NH (US); Rafal Jezierski, Boston, MA (US); Roger R. Cassidy, Jr., Methuen, MA (US)

(73) Assignee: Smith & Nephew, Inc., Memphis, TN (US)

( * ) Notice: Subject to any disclaimer, the term of this patent is extended or adjusted under 35 U.S.C. 154(b) by 262 days.

This patent is subject to a terminal disclaimer.

(21) Appl. No.: 13/051,257

(22) Filed: Mar. 18, 2011

(65) Prior Publication Data

US 2011/0230904 A1 Sep. 22, 2011

Related U.S. Application Data

(63) Continuation of application No. 11/734,674, filed on Apr. 12, 2007, now Pat. No. 7,922,737, which is a continuation of application No. 09/983,810, filed on Oct. 26, 2001, now Pat. No. 7,226,459.

(51) Int. Cl.
*A61B 17/32* (2006.01)
*A61B 10/00* (2006.01)

(52) U.S. Cl.
USPC ........................... 606/170; 606/180; 600/566

(58) Field of Classification Search
USPC ........................... 606/170, 180; 600/566, 567
See application file for complete search history.

(56) References Cited

U.S. PATENT DOCUMENTS

| | | | |
|---|---|---|---|
| 1,831,786 A | 4/1926 | Duncan |
| 1,585,934 A | 5/1926 | Joseph |
| 1,666,332 A | 4/1928 | Hirsch |
| 2,708,437 A | 5/1955 | Hutchins |
| 3,686,706 A | 8/1972 | Finley |

(Continued)

FOREIGN PATENT DOCUMENTS

| | | |
|---|---|---|
| DE | 3206381 | 9/1983 |
| DE | 3601453 | 9/1986 |

(Continued)

OTHER PUBLICATIONS

Defendant Hologic Inc.'s Preliminary, Non-Binding List of Asserted Prior Art References in *Smith & Nephew, Inc. v. Hologic, Inc.*, Civil Action Nos. 11-CV-12064-RWZ and 10-CV-10951-RWZ, U.S. District Court for the District of Massachusetts, Feb. 8, 2012, 8 pages.

(Continued)

*Primary Examiner* — Julian W Woo
(74) *Attorney, Agent, or Firm* — Nixon Peabody LLP

(57) ABSTRACT

A surgical instrument includes a cutting member with an implement for cutting tissue, and a drive coupled to the cutting member to simultaneously rotate and translate the cutting member in response to a force applied to the drive. A method of cutting tissue includes positioning an outer member such that tissue is located within the outer member, engaging the tissue with an inner member, and simultaneously rotating and translating the inner member to cut the tissue. A tangential cutting force is applied to the tissue with the inner member to mechanically cut the tissue. The inner member is mechanically driven to undergo simultaneous rotation and translation.

14 Claims, 14 Drawing Sheets

(56) References Cited

U.S. PATENT DOCUMENTS

| | | |
|---|---|---|
| 3,734,099 A | 5/1973 | Bender et al. |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,261,346 A | 4/1981 | Wettermann |
| 4,316,465 A | 2/1982 | Dotson |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,589,414 A | 5/1986 | Yoshida et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,037,386 A | 8/1991 | Marcus et al. |
| 5,106,364 A | 4/1992 | Hayafuji et al. |
| 5,112,299 A | 5/1992 | Pascaloff |
| 5,116,868 A | 5/1992 | Chen et al. |
| 5,133,713 A | 7/1992 | Huang et al. |
| 5,152,744 A | 10/1992 | Krause et al. |
| 5,163,433 A | 11/1992 | Kagawa et al. |
| 5,176,677 A | 1/1993 | Wuchinich |
| 5,195,541 A | 3/1993 | Obenchain |
| 5,226,910 A | 7/1993 | Kajiyama et al. |
| 5,269,785 A | 12/1993 | Bonutti |
| 5,275,609 A | 1/1994 | Pingleton et al. |
| 5,304,118 A | 4/1994 | Trese et al. |
| 5,312,399 A | 5/1994 | Hakky et al. |
| 5,312,425 A | 5/1994 | Evans et al. |
| 5,320,091 A | 6/1994 | Grossi et al. |
| 5,350,390 A | 9/1994 | Sher |
| 5,364,395 A | 11/1994 | West |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,411,513 A | 5/1995 | Ireland et al. |
| 5,425,376 A | 6/1995 | Banys et al. |
| 5,429,601 A | 7/1995 | Conley et al. |
| 5,443,476 A | 8/1995 | Shapiro |
| 5,449,356 A | 9/1995 | Walbrink et al. |
| 5,456,689 A | 10/1995 | Kresch et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,569,254 A | 10/1996 | Carlson et al. |
| 5,569,284 A | 10/1996 | Young et al. |
| 5,591,187 A | 1/1997 | Dekel |
| 5,601,583 A | 2/1997 | Donahue et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,676,497 A | 10/1997 | Kim |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,282 A | 9/1998 | Fowler |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,358,263 B2 | 3/2002 | Mark et al. |
| 6,402,701 B1 | 6/2002 | Kaplan et al. |
| 6,428,486 B2 | 8/2002 | Ritchart et al. |
| 6,494,892 B1 | 12/2002 | Ireland et al. |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |

(56) References Cited

U.S. PATENT DOCUMENTS

| | | | |
|---|---|---|---|
| 7,025,732 B2 | 4/2006 | Thompson et al. | |
| 7,226,459 B2 | 6/2007 | Cesarini et al. | |
| 7,922,737 B1 * | 4/2011 | Cesarini et al. | 606/170 |
| 2001/0039963 A1 | 11/2001 | Spear et al. | |
| 2001/0047183 A1 | 11/2001 | Privitera et al. | |
| 2003/0050638 A1 | 3/2003 | Yachia et al. | |
| 2003/0078609 A1 | 4/2003 | Finlay et al. | |
| 2003/0114875 A1 | 6/2003 | Sjostrom | |
| 2006/0241586 A1 | 10/2006 | Wilk | |

FOREIGN PATENT DOCUMENTS

| | | |
|---|---|---|
| DE | 4038398 A1 | 6/1992 |
| DE | 4440035 A1 | 5/1996 |
| DE | 19633124 | 5/1997 |
| EP | 0310285 A2 | 4/1989 |
| EP | 0327410 | 8/1989 |
| EP | 0557044 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| GB | 2093353 | 9/1982 |
| GB | 2311468 A | 10/1997 |
| WO | 81/01648 A1 | 6/1981 |
| WO | 92/11816 A3 | 7/1992 |
| WO | 93/07821 | 4/1993 |
| WO | 93/15664 | 8/1993 |
| WO | WO9426181 A1 | 11/1994 |
| WO | 95/05777 A1 | 3/1995 |
| WO | 95/10981 A1 | 4/1995 |
| WO | 95/30377 | 11/1995 |
| WO | 96/11638 | 4/1996 |
| WO | 96/26676 A1 | 9/1996 |
| WO | 97/09922 A1 | 3/1997 |
| WO | 97/17027 A1 | 5/1997 |
| WO | 97/19642 A1 | 6/1997 |
| WO | 97/24071 A1 | 7/1997 |
| WO | 97/34534 A1 | 9/1997 |
| WO | 97/35522 A1 | 10/1997 |
| WO | 98/09569 A1 | 3/1998 |
| WO | 98/10707 A1 | 3/1998 |
| WO | 98/46147 A1 | 10/1998 |
| WO | 99/03407 A1 | 1/1999 |
| WO | 99/03409 A1 | 1/1999 |
| WO | 99/07295 A1 | 2/1999 |
| WO | 99/39648 A1 | 8/1999 |
| WO | 99/44506 A1 | 9/1999 |
| WO | 99/60935 A1 | 12/1999 |
| WO | WO0012010 A1 | 3/2000 |
| WO | 00/33743 A1 | 6/2000 |
| WO | 00/44295 A1 | 8/2000 |
| WO | 00/47116 A1 | 8/2000 |
| WO | WO0057797 A1 | 10/2000 |
| WO | 01/35831 A1 | 5/2001 |
| WO | 01/58368 A1 | 8/2001 |
| WO | 01/95810 A2 | 12/2001 |
| WO | 02/069808 A2 | 9/2002 |
| WO | 03/077767 A1 | 9/2003 |
| WO | 2005/060842 A1 | 7/2005 |
| WO | 2005/096963 A2 | 10/2005 |
| WO | 2006/121968 A2 | 11/2006 |
| WO | 2006/121970 A2 | 11/2006 |
| WO | 2007/044833 A2 | 4/2007 |

OTHER PUBLICATIONS

Baggish et al., "Instrumentation for Hysteroscopy," in "Diagnostic and Operative Hysterectomy," Mosby (1999).

Fishing Reel produced by Shimano of Japan into the U.S. prior to Oct. 26, 2001, 7 pages.

Hologic's Opposition to Smith & Nephew's Motion for Preliminary Injunction, Redacted, *Smith & Nephew, Inc.* v. *Hologic, Inc.*, Civil Action No. 11-CV-12064-RWZ, filed Dec. 30, 2011, 26 pages.

Exhibit P to Hologic's Opposition to Smith & Nephew's Motion for Preliminary Injunction, Redacted, *Smith & Nephew, Inc.* v. *Hologic, Inc.*, Civil Action No. 11-CV-12064-RWZ, filed Dec. 30, 2011, 99 pages.

Dictionary definition of reciprocate, Merriam-Webster Dictionary, on-line edition, retrieved Mar. 20, 2013.

Dictionary definition of rotate, Merriam-Webster Dictionary, on-line edition, retrieved Mar. 20, 2013.

Dictionary definition of translate, Merriam-Webster Dictionary, on-line edition, retrieved Mar. 20, 2013.

Decision Granting Request for Reexam mailed Jun. 5, 2012.

Office Action for U.S. Appl. No. 95/001,933 mailed Jun. 5, 2012.

Patent Owner's Response to Office Action for U.S. Appl. No. 95/001,933 mailed Jun. 5, 2012.

Third Party Requester's Response to Office Action for U.S. Appl. No. 95/001,933 mailed Jun. 5, 2012.

Office Action for U.S. Appl. No. 95/001,933 mailed Apr. 1, 2013.

Patent Owner's Response to Office Action for U.S. Appl. No. 95/001,933 mailed Apr. 1, 2013.

Third Party Requester's Response to Office Action for U.S. Appl. No. 95/001,933 mailed Apr. 1, 2013.

Office Action for U.S. Appl. No. 95/001,933 mailed Sep. 19, 2013.

Patent Owner's Response to Office Action for U.S. Appl. No. 95/001,933 mailed Sep. 19, 2013.

* cited by examiner

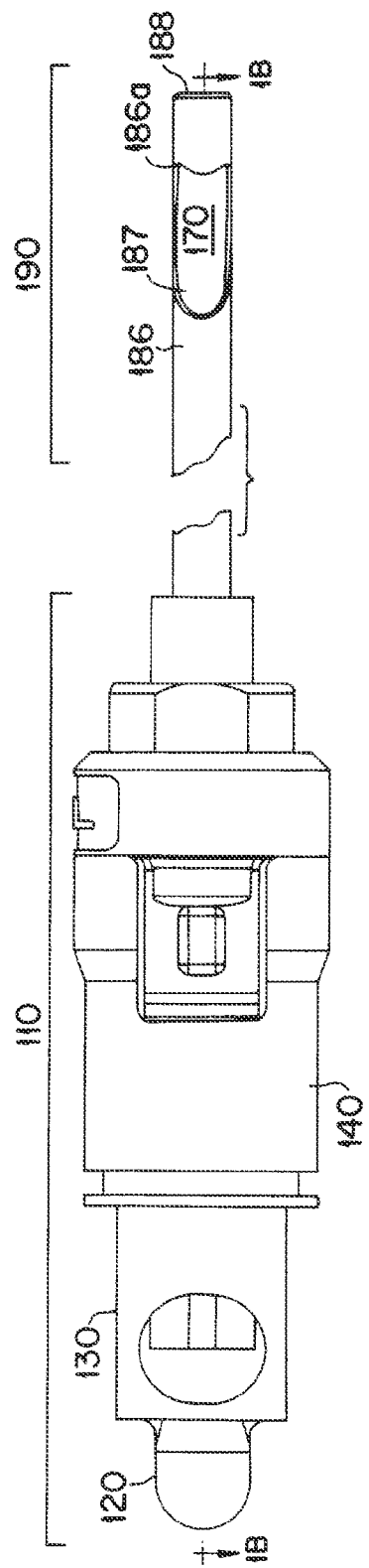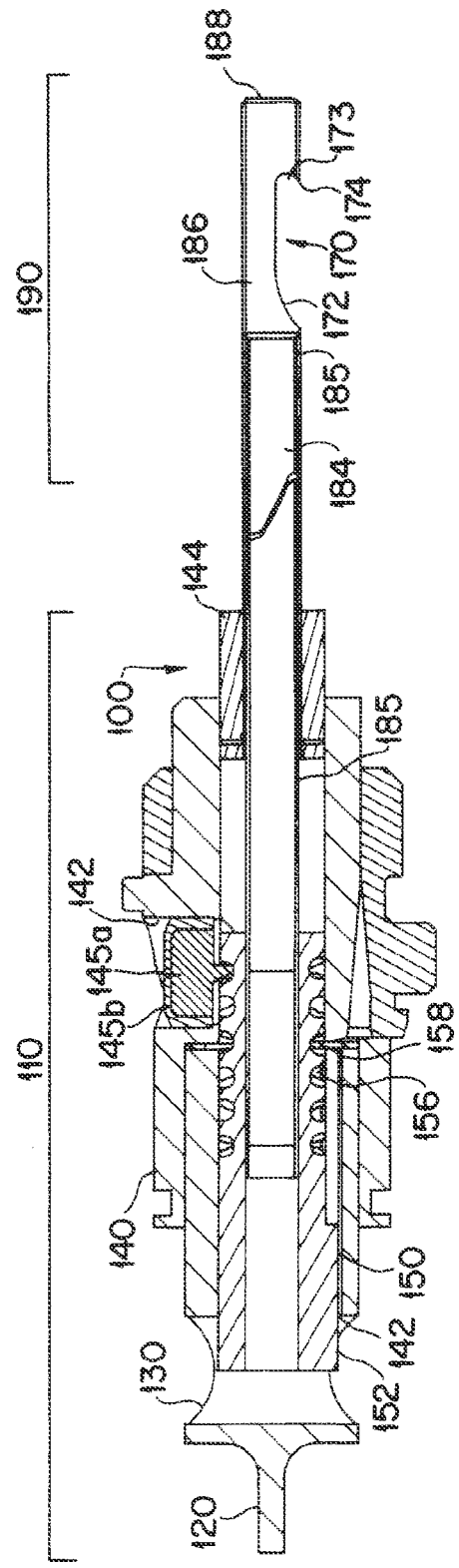
FIG. 1A
FIG. 1B

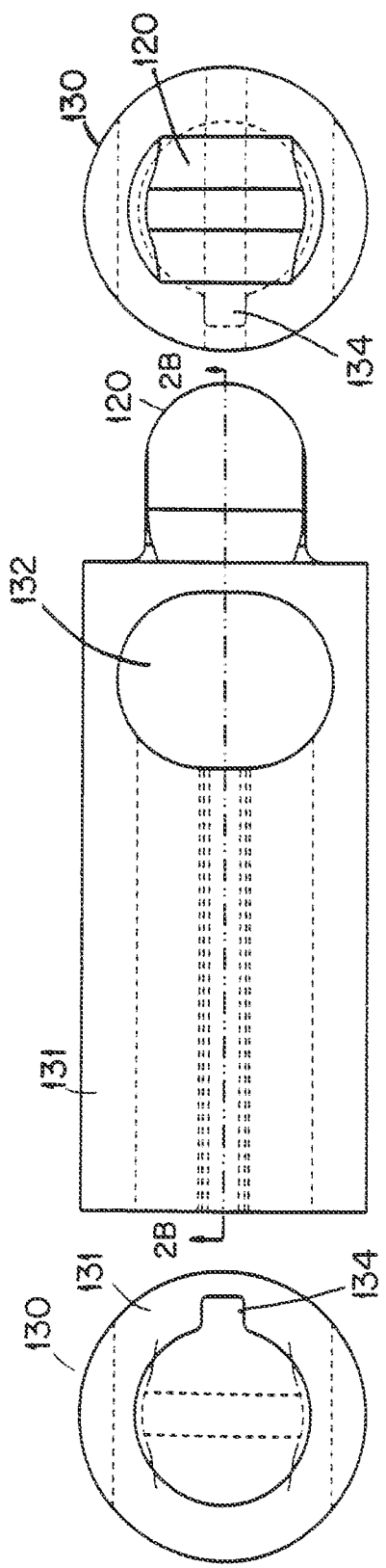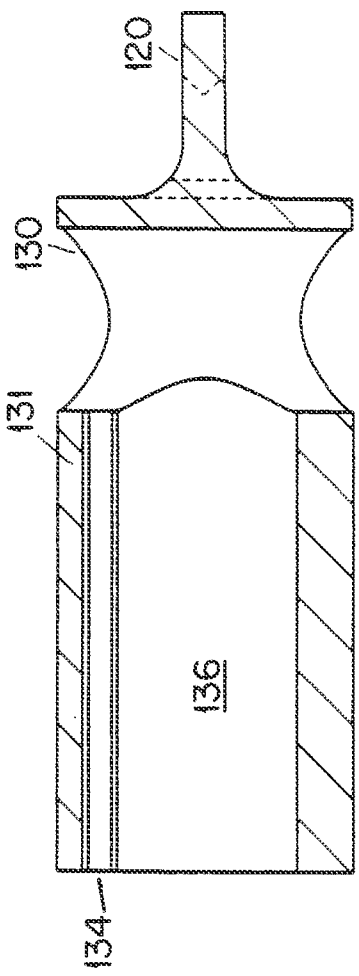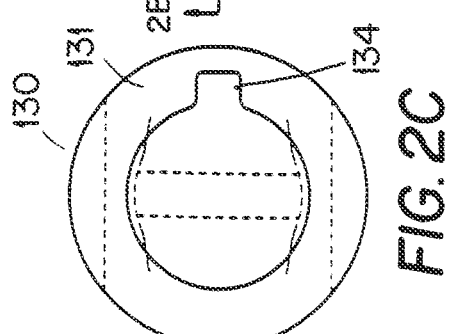

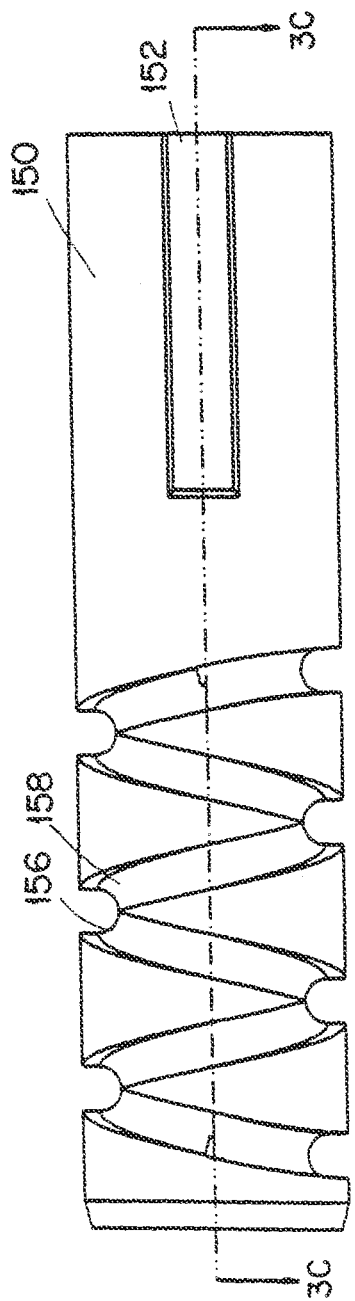
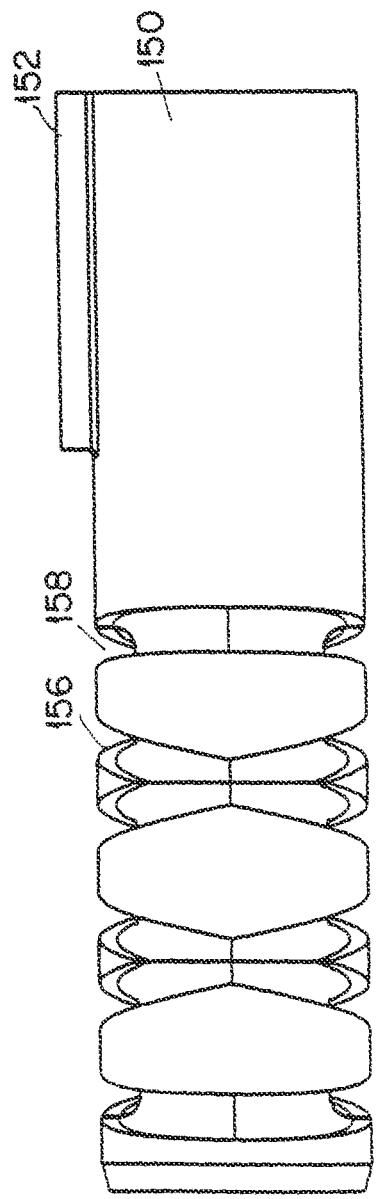
FIG. 3A
FIG. 3B

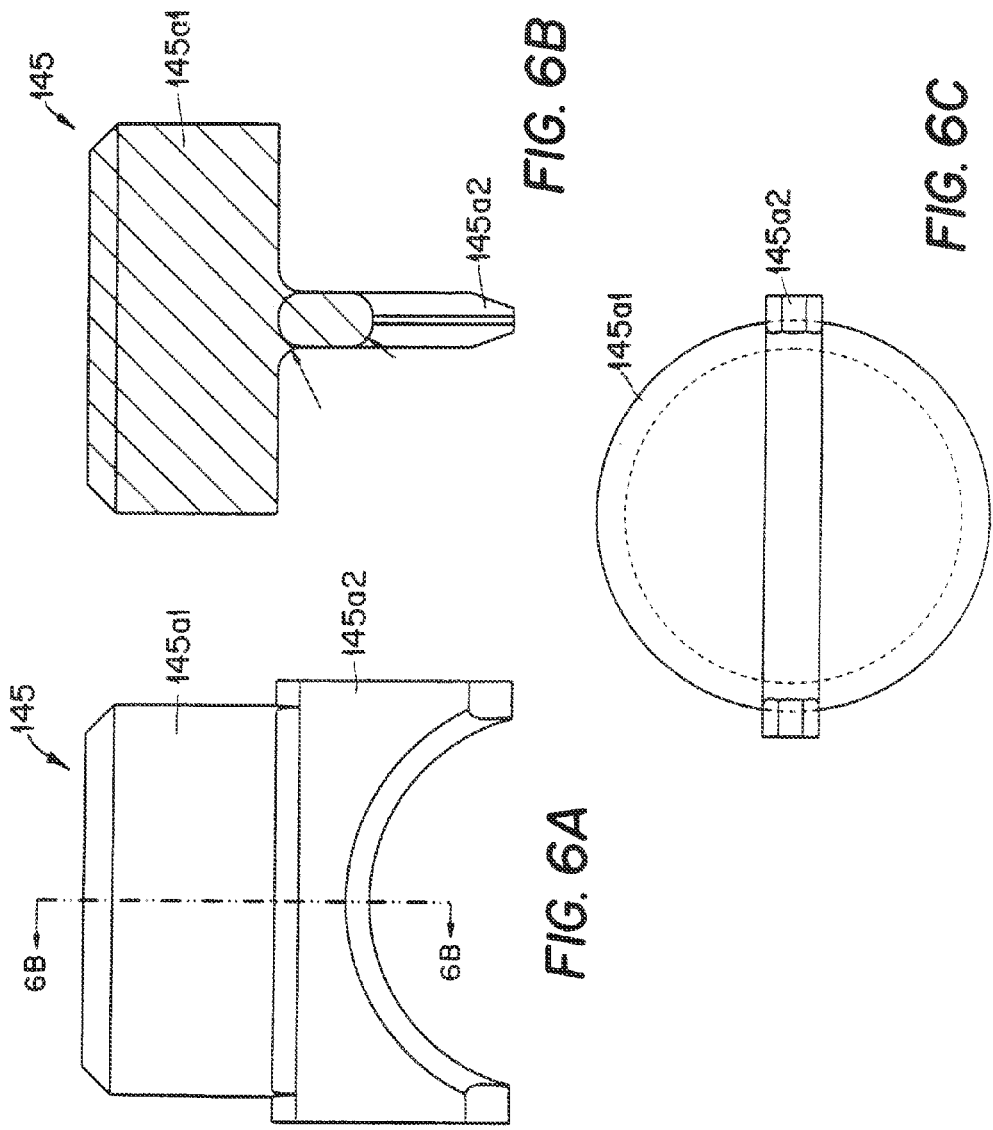

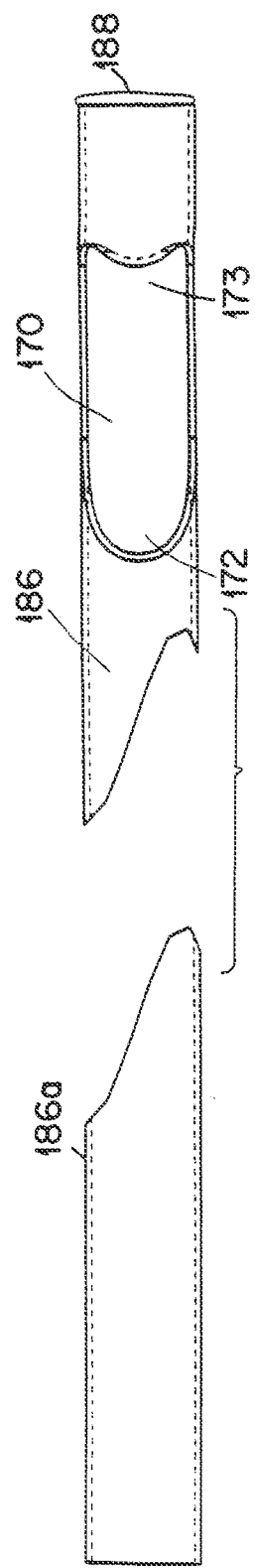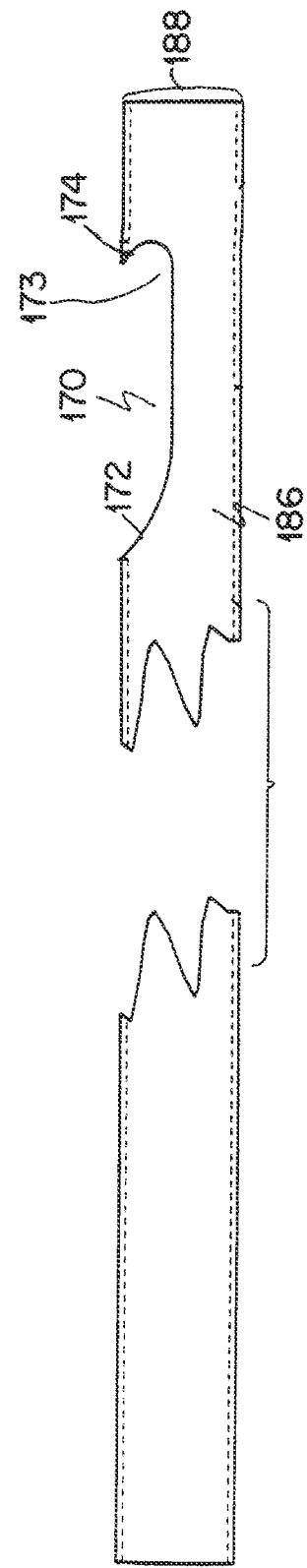

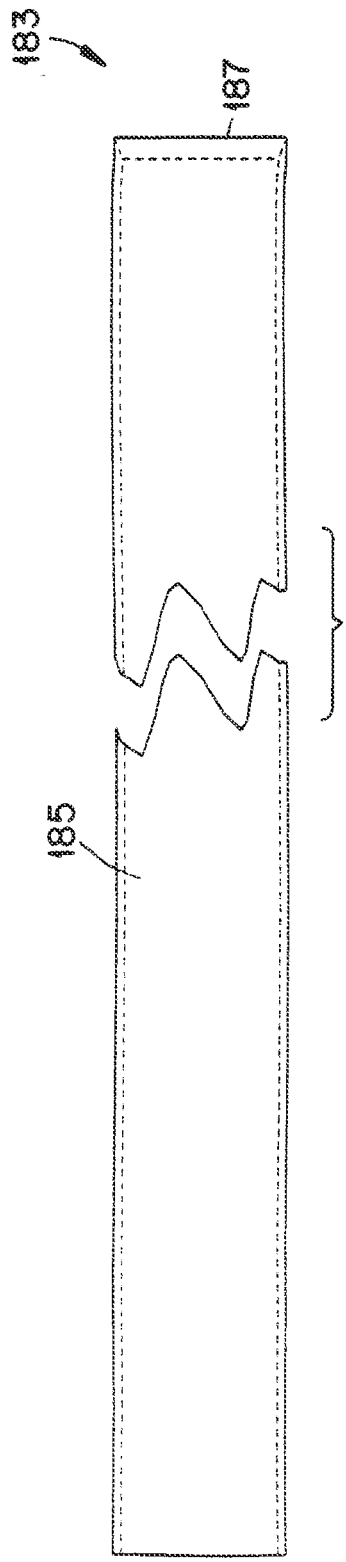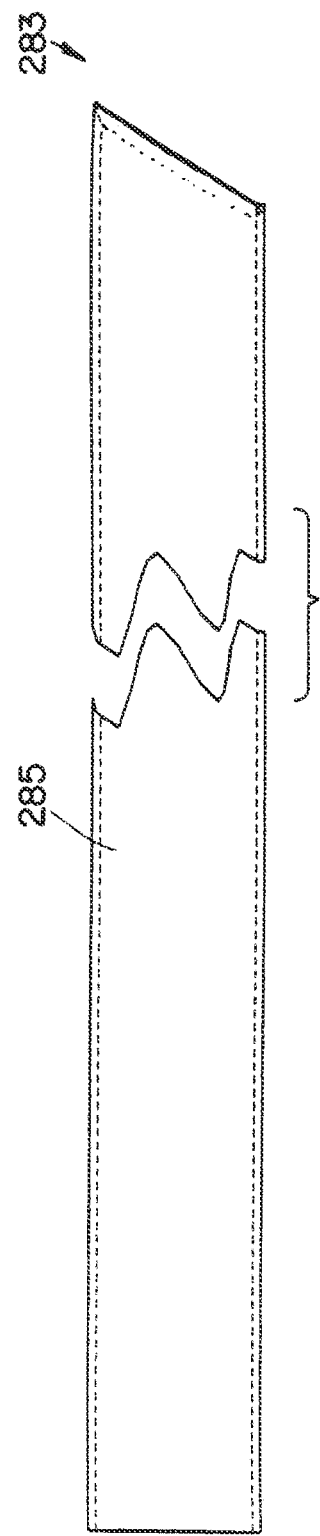
FIG. 9
FIG. 11

RECIPROCATING ROTARY ARTHROSCOPIC SURGICAL INSTRUMENT

CROSS REFERENCE TO RELATED APPLICATION

This application is a continuation of U.S. patent application Ser. No. 11/734,674, filed Apr. 12, 2007, now allowed, which is a continuation of U.S. application Ser. No. 09/983,810, filed Oct. 26, 2001, now U.S. Pat. No. 7,226,459. The prior applications are incorporated herein by reference in their entirety.

TECHNICAL FIELD

This invention relates to rotary cutting surgical instruments, and more particularly, to a reciprocating rotary surgical instrument for cutting semi-rigid tissue.

BACKGROUND

Conventional arthroscopic surgical instruments generally include an outer tube and an inner member that rotates or translates axially within the outer tube. The outer tube and inner member may interact to create shear forces that cut tissue. This type of cutting is generally used to cut soft tissue, such as muscle, ligaments, and tendons.

SUMMARY

In one aspect, a surgical instrument includes a cutting member with an implement for cutting tissue, and a drive coupled to the cutting member to simultaneously rotate and translate the cutting member in response to a force applied to the drive.

One or more of the following features may be included in the surgical instrument. The drive is configured such that the cutting member reciprocates. The drive includes a drive member attached to the cutting member. The drive member includes a helical groove. The drive includes a translation piece disposed in the groove such that rotary driving of the drive member results in simultaneous reciprocation of the drive member relative to the translation piece.

In the illustrated embodiment, the drive includes an inner drive hub coupled to the drive member. The inner drive hub defines a slot and the drive member includes a key received in the slot rotary coupling the drive member to the inner drive hub such that the drive member rotates with the inner drive hub while being free to translate relative to the inner drive hub. The helical groove includes a left-hand threaded helical channel. The helical groove includes a right-hand threaded helical channel. The cutting member is attached to the drive member to move rotatably and axially with the member.

The implement is a chamfered cutting edge at a distal end of the cutting member. The chamfered edge is a straight cutting edge. Alternatively, the chamfered edge is an angled cutting edge.

The instrument includes an outer tubular member. The cutting member is received within the outer member. The outer member includes a cutting window disposed proximate to a tip of the outer member. The cutting window is an opening in the outer member exposing the cutting member to tissue. The cutting window has a U-shaped proximal end and a saddle-shaped distal end. The saddle-shaped distal end of the cutting window includes a hook.

The translation piece includes a follower received within the groove and a sealing cap over the follower. The follower is free to swivel relative to the sealing cap. The follower has an arched bridge shape. The translation piece is coupled to the drive member such that the translation piece is disposed in the helical groove and swivels to follow the helical groove as the drive member rotates.

In another aspect, a method of cutting tissue includes positioning an outer member such that tissue is located within the outer member, engaging the tissue with an inner member received within the outer member, and simultaneously rotating and translating the inner member to cut the tissue. One or more of the following features may be included. The translating is reciprocating. The outer member is oriented tangentially to the tissue.

In another aspect, a method of cutting tissue includes providing a surgical instrument having an outer member and an inner member received within the outer member for movement relative to the outer member, and applying a tangential cutting force to the tissue with the inner member to mechanically cut the tissue.

In another aspect, a method of cutting tissue includes applying a tangential cutting force to tissue with a member, and mechanically driving the member to undergo simultaneous rotation and translation. The method may include that the translation is reciprocation.

The cutting edge of conventional arthroscopic surgical instruments, such as rotary shears, have difficulty initiating a cut into semi-rigid tissue tend to bounce away from the tissue. Toothed edge geometry somewhat ameliorates this problem because the "teeth" attempt to pierce the tissue to initiate a cut. However, the efficiency of using "teeth" is limited and the limitations are more evident when cutting large volumes of semi-rigid tissue, such as meniscus or intrauterine fibroid tissue. The simultaneous rotating and reciprocating inner member of the surgical instrument of the invention overcomes these difficulties. The tangential approach to the tissue in the method of the invention limits the tendency of the instrument to bounce away from the tissue. In particular, the instrument and method provide a higher resection rate to shorten procedure length, during, e.g., fibroid and polyp resection.

The details of one or more implementations are set forth in the accompanying drawings and the description below. Other features will be apparent from the description and drawings, and from the claims.

DESCRIPTION OF DRAWINGS

FIG. 1A is a side view and 1B is a cross-sectional view taken along 1B-1B in FIG. 1A of a reciprocating rotary surgical instrument.

FIG. 2A is a top view, FIG. 2B is a cross-sectional view taken along 2B-2B in FIG. 2A, FIG. 2C is a distal end view, and FIG. 2D is a proximal end view of the inner drive hub of the reciprocating rotary surgical instrument of FIG. 1.

FIG. 3A is a top view, FIG. 3B is a side view.

FIG. 6A is a side view, FIG. 6B is a cross-sectional view taken along 6B-6B in FIG. 6A, and FIG. 6C is a top view of the follower of the translation piece of the reciprocating rotary surgical instrument of FIG. 1.

FIG. 8A is a top view and FIG. 8B is a side view of the outer member of the reciprocating rotary surgical instrument of FIG. 1.

FIG. 9 is a side view of the inner member of the reciprocating rotary surgical instrument of FIG. 1.

FIG. 11 is a side view of an alternate implementation of the inner member of a reciprocating surgical instrument.

Like reference symbols in the various drawings indicate like elements.

DETAILED DESCRIPTION

Figure 3C:
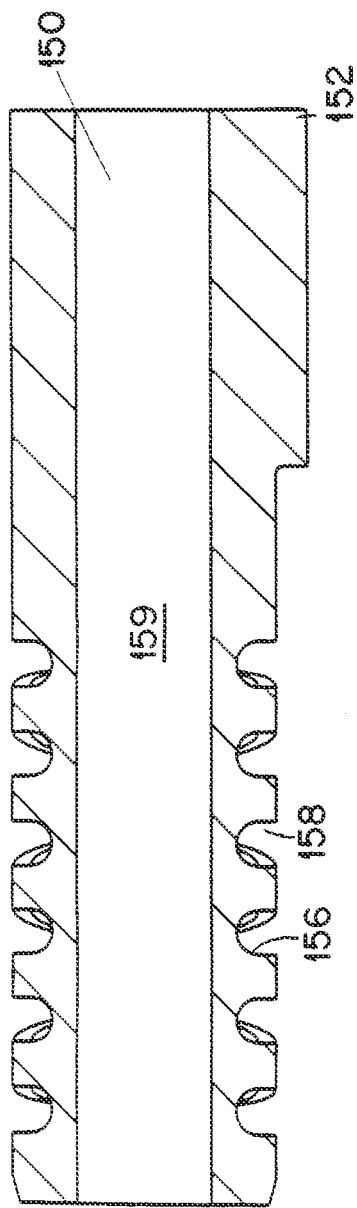
FIG. 3C is a cross-sectional view taken along 3C-3C in FIG. 3A.
Figure 3D:
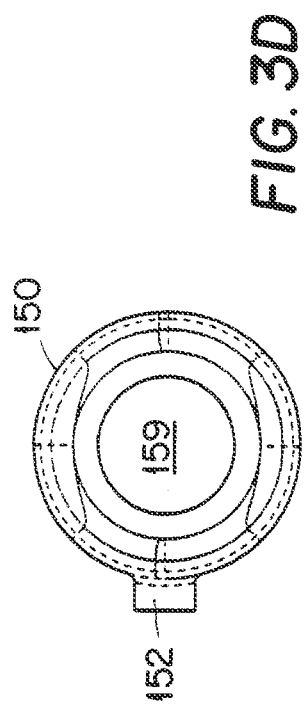
FIG. 3D is a proximal end view of the helical member of the reciprocating rotary surgical instrument of FIG. 1.

As shown in FIGS. 1A and 1B, a cutting device 100 includes a driving end 110 and a cutting end 190. The driving end 110 is located at the proximal end of the cutting device 100. The cutting end 190 is located at the distal end of the cutting device 100.

At the driving end 110, there is an inner drive hub 130 with a drive coupler 120, and an outer hub 140. The drive coupler 120 mounts into a rotary driver (not shown), which turns the drive coupler 120 causing a helical member 150 and the inner drive hub 130 to rotate. For instance, the rotary driver is Dyonics Power Handpiece, No. 725355. The inner drive hub 130 with the drive coupler 120 is, for example, a component of Smith & Nephew disposable arthroscopic surgical instrument, No. 7205306. The helical member 150 is located within the inner drive hub 120 and the outer hub 140. The helical member 150 and a translation piece 145 are coupled together such that rotation of the helical member 150 causes linear translation of the helical member 150, as described further below.

The cutting device 100 includes an elongated inner member 185 and an elongated outer member 186, as shown in FIG. 1B. The inner member 185 is tubular with a hollow interior 184. The inner member 185 is fixed to the helical member 150 for axial and rotary motion therewith.

The outer member 186 is also tubular with a hollow interior 187. The inner member 185 is received inside the outer member 186. The outer member 186 is fixed to the outer hub 140 and does not move. The outer member 186 includes a tip 188, which is blunt, i.e., the corners are rounded. At the cutting end 190, the outer member 186 defines a cutting window 170 through a wall 186a of the outer member 186.

Referring to FIGS. 2A-2D, the inner drive hub 130 includes the drive coupler 120, a lumen 136, an aspiration opening 132, and a slot 134. The drive coupler 120 extends from the proximal end of the inner drive hub 130 and mounts in the rotary driver. Debris from the cutting end 190 of the cutting device 100 is aspirated through the aspiration opening 132. The slot 134 is disposed in a wall 131 of the inner drive hub 130. The slot 134 is like a track along one side of the inner drive hub 130. The slot 134 of the inner drive hub 130 is coupled with a key 152 of the helical member 150 (see FIG. 4B) so that rotation of the inner drive hub 130 causes the helical member 150 to rotate while allowing the helical member 150 to move axially relative to the inner drive hub 130, e.g., the key 152 axially slides along the slot 134.

Referring to FIGS. 3A-3D, the helical member 150 of the cutting device 100 is formed of a lubricious material in a tubular shape with a through lumen 159. The inner member 185 is disposed within the helical member 150 and fixed therein, for example, by epoxy, injection-molded, or overmolded plastic.

The helical member 150 includes the key 152 and two helical channels 156, 158 disposed thereon. As shown in FIG. 3B, the key 152 is shaped like a fin and is located at the proximal end of the helical member 150. The key 152 mates with the slot 134 of the inner drive hub 130.

The two helical channels 156, 158 are disposed on a distal portion of the exterior surface of the helical member 150. One helical channel 156 is right-hand threaded; the other helical channel 158 is left-hand threaded. The pitch of the helical channels may be different or the same. The length of the distal portion of the helical member 150 with helical channels 156, 158 is longer than the length of the cutting window 170. The helical channels 156, 158 are smoothly blended together at their ends to form a continuous groove so that there is a smooth transition from one helical channel to the other helical channel at each end of the distal portion of the helical member 150.

The helical member 150 and the inner drive hub 130 are mechanically driven by the rotary driver. The helical member 150 also moves in an axial direction, e.g., reciprocates, as a result of the interaction of the translation piece 145 with the helical channels 156, 158, as described below.

Figure 4A:
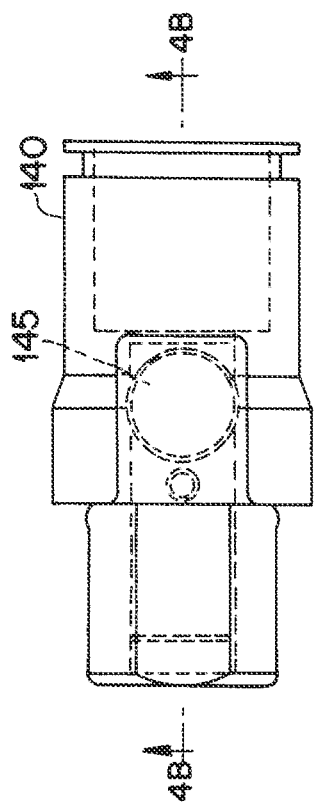
FIG. 4A is a top view.
Figure 4B:
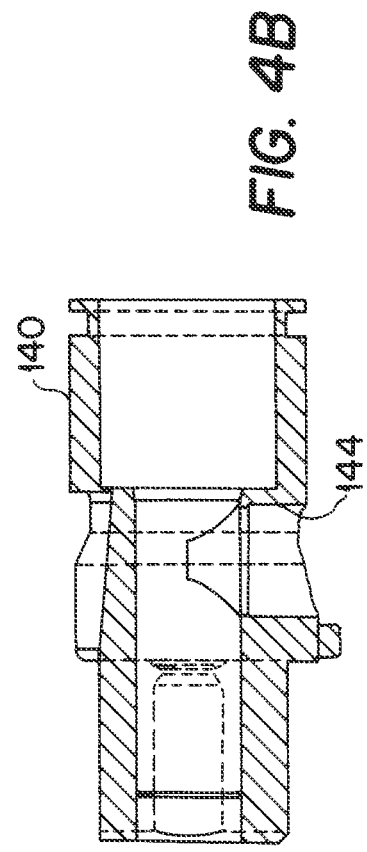
FIG. 4B is a cross-sectional view taken along 4B-4B in FIG. 4A.
Figure 4C:
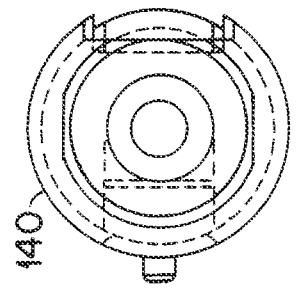
FIG. 4C is a distal end of the outer hub of the reciprocating rotary surgical instrument of FIG. 1.

Referring to FIGS. 4A-4C, the outer hub 140 of the cutting device 100 is formed of hard plastic and does not move. An example of an outer hub is a component of Smith & Nephew disposable arthroscopic surgical instrument, No. 7205306, modified with a cutout 144 for receiving the translation piece 145. The cutout 144 is disposed within a wall of the outer hub 140, for example, centrally, as in FIG. 4B, and aligned with the helical member. The translation piece 145 is located in the cutout 144 of the outer hub 140.

As shown in FIG. 1B, the outer member 186 is disposed within the outer hub 140 and fixed therein by a coupling 144 using, for example, epoxy, glue, insert molding, or spinwelding.

Figure 5A:
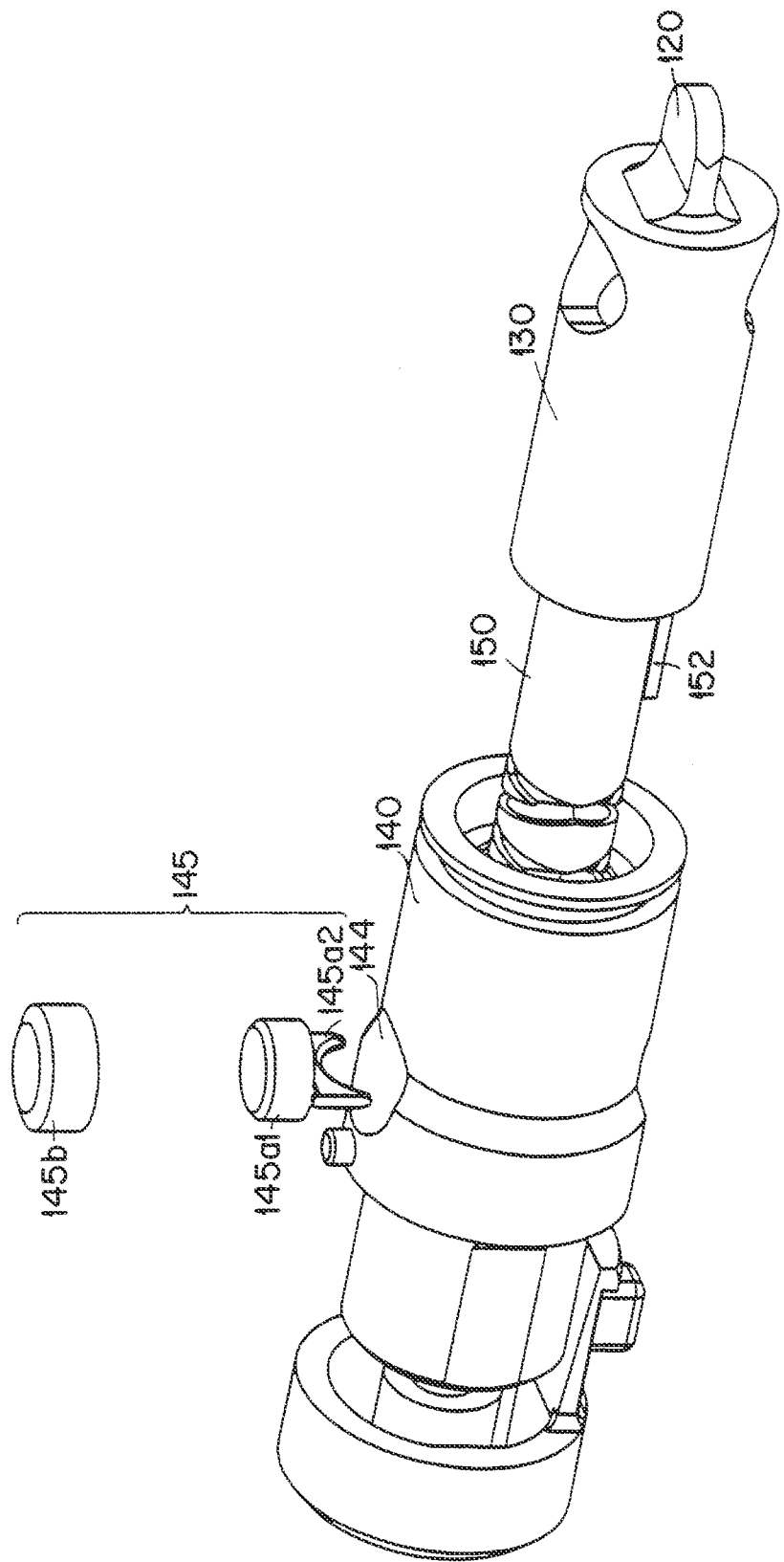
FIG. 5A is an exploded view.

Referring to FIG. 5A, the translation piece 145 includes a follower 145a and a cap 145b. Having the two helical channels 156, 158 in conjunction with the slot/key 134, 152 coupling of the inner drive hub 130 and the helical member 150, the rotary driver only needs to rotate in one direction and does not require reversal of the rotational direction upon the translation piece 145 reaching the end of one of the helical channels 156, 158.

Figure 5B:
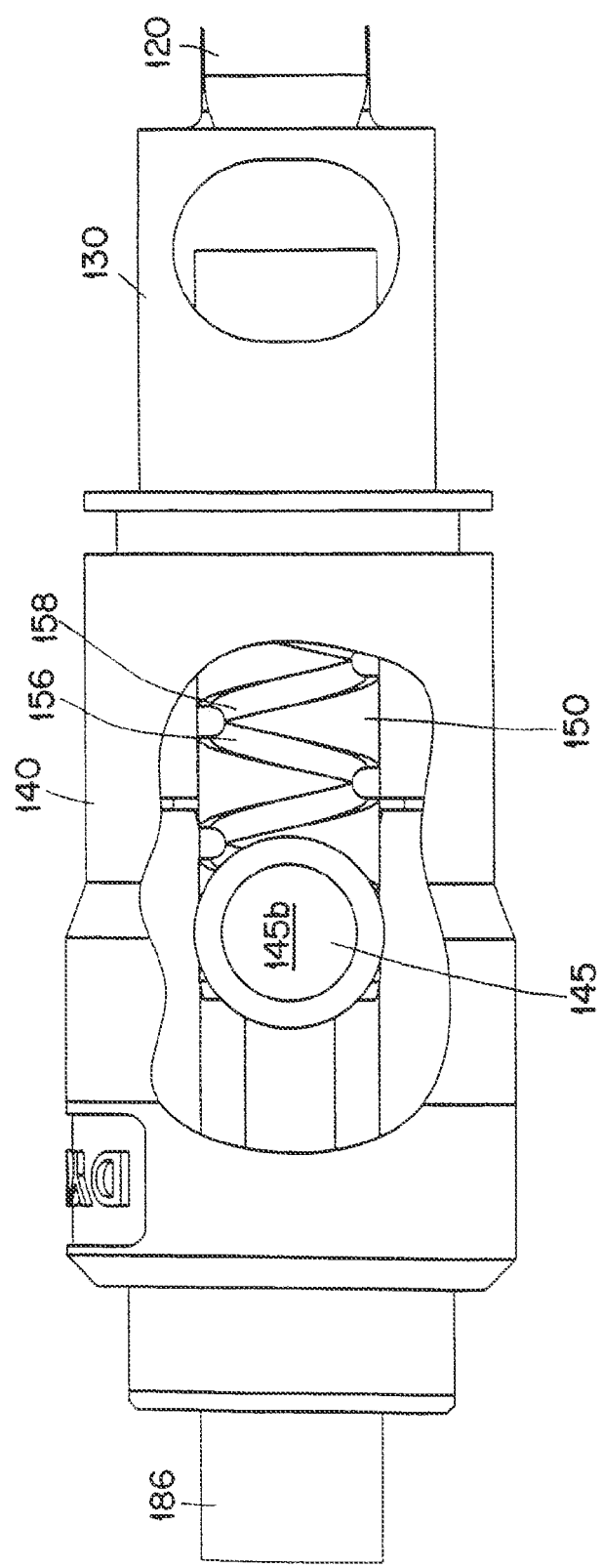
FIG. 5B is a partial cutaway view.
Figure 5C:
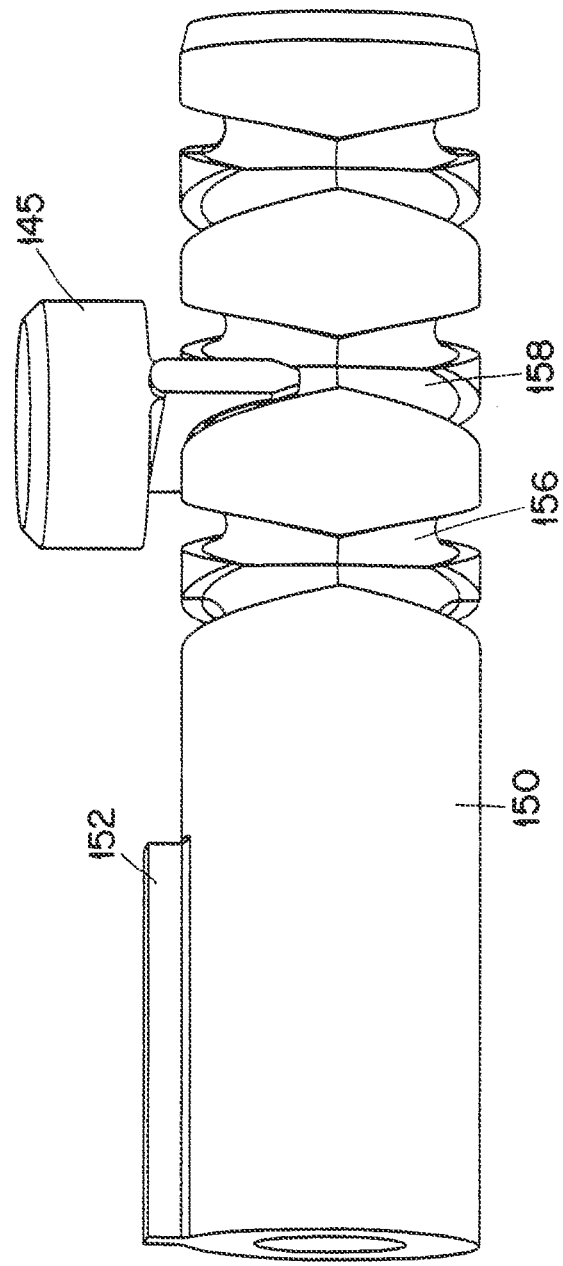
FIGS. 5C and 5D are side views of the translation piece and the helical member of the surgical instrument of FIG. 1.
Figure 5D:
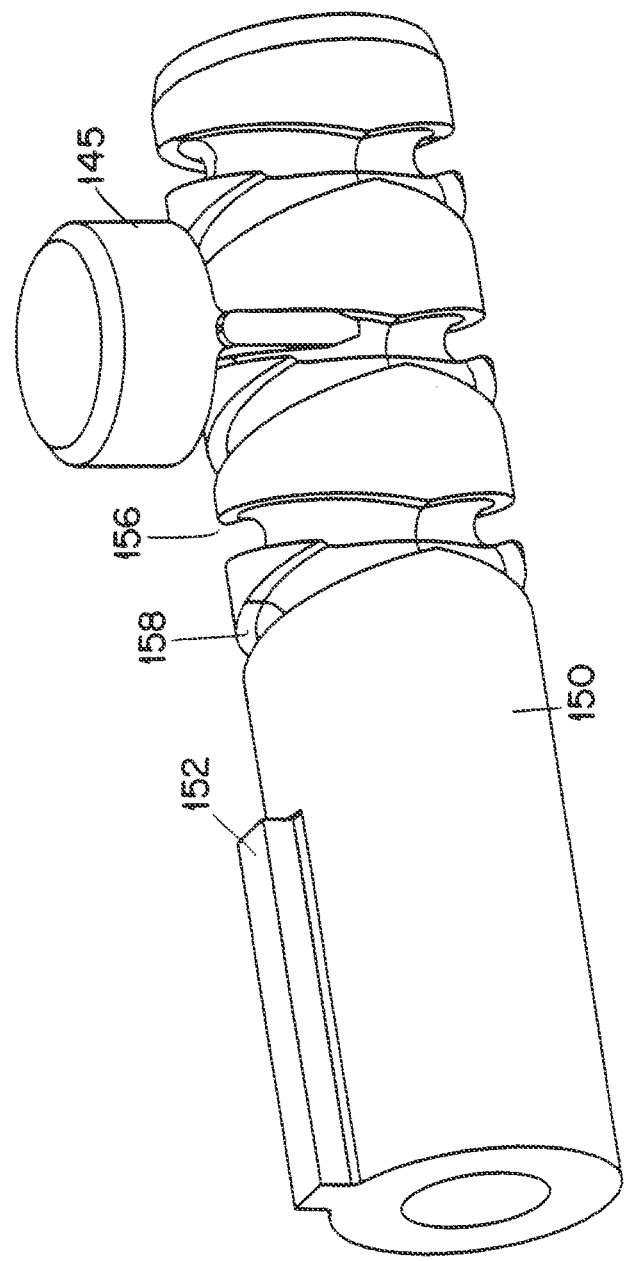

Referring to FIGS. 6A-6C, the follower 145a includes a cylindrical head 145a1 and two legs 145a2. As shown in FIGS. 5B-5D, the legs 145a2 form an arch and rest in the channels of the double helix 156, 158 formed in the distal portion of the exterior surface of the helical member 150. The arch of the legs 145a2 is dimensionally related to the diameter described by the helical channels 156, 158 of the helical member 150.

Referring particularly to FIGS. 5C and 5D, as the helical member 150 and the inner drive hub 130 are mechanically driven by the rotary driver (not shown), the follower 145a follows the helical channels 156, 158, swiveling as the follower 145a smoothly transitions from helical channel to helical channel 156,158 at the ends of the distal portion of the helical member 150 having the helical channels 156, 158. The coupling of the follower 145a to the helical channels 156, 158 causes the helical member 150 to also translate. Thus, the inner member 185 simultaneously rotates and reciprocates to cut the tissue.

Figure 7B:
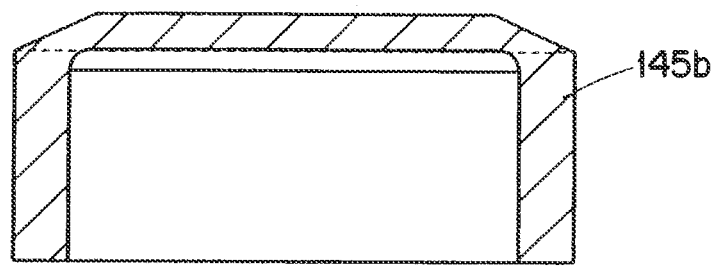
FIG. 7A is a top view and FIG. 7B is a cross-sectional view taken along 7B-7B of FIG. 7A of the cap for the follower of the translation piece of the reciprocating rotary surgical instrument of FIG. 1.
Figure 7A:
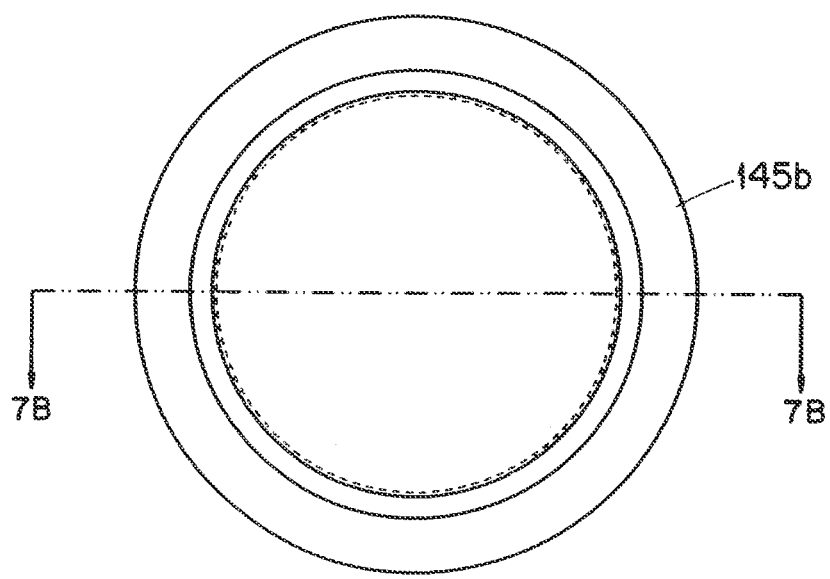

Referring to FIGS. 7A and 7B, the cap 145b of the translation piece 145 covers the follower 145a to provide a seal to allow sufficient suction to remove aspirated debris. Also, the cap 145b is a separate piece from the follower 145a in order to allow the follower 145b to swivel.

As shown in FIGS. 8A and 8B, the outer member cutting window 170 has a generally oblong shape. The proximal end 172 of the cutting window 170 is U-shaped and the distal end 173 has a saddle shape that forms a hook 174. The distal end 173 is chamfered to provide a sharp edge. The hook 174 pierces the targeted tissue to hold the tissue as the inner member 185 cuts. Also, the shape of the cutting window 170 eliminates galling between the inner and outer members 185, 186, and dulling of the cutting edge of the inner member 185.

The cutting window 170 is disposed proximate to the tip 188 of the outer member 186. The cutting window 170 exposes the inner member 185 over a length L.

Figure 10:
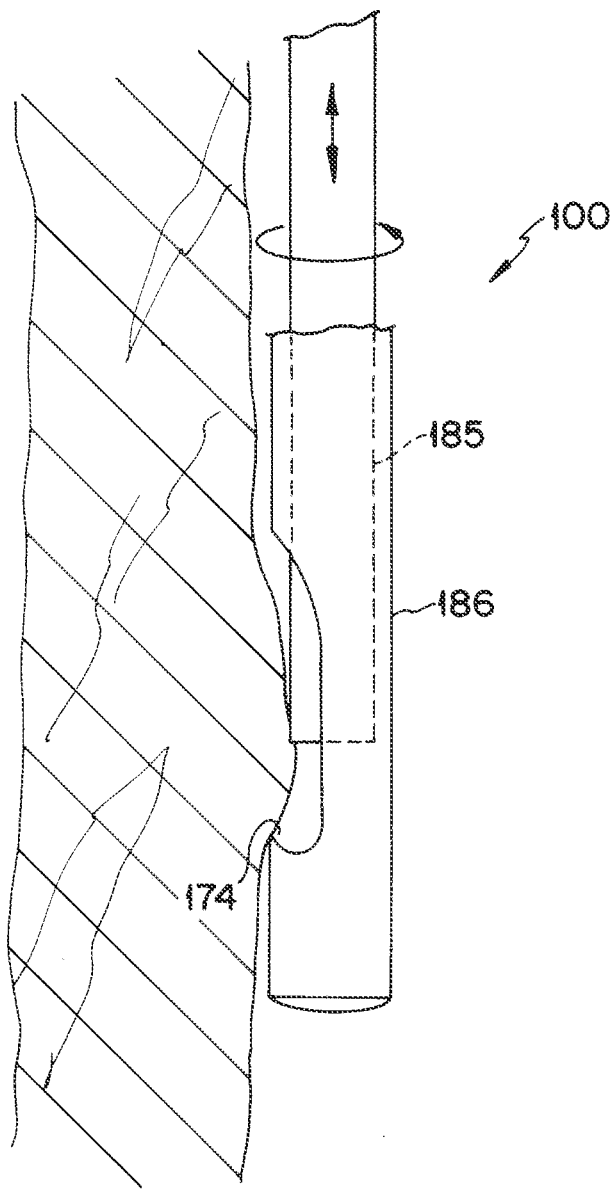
FIG. 10 illustrates a reciprocating rotary surgical instrument of FIG. 1 in use to cut tissue.

FIG. 9 shows that the inner member 185 is generally tubular with hollow interior 187. Aspiration of debris occurs through the hollow interior 187 of the inner member 185, and through the lumen of the helical member to the aspiration opening 132 of the inner drive hub 130. The distal end 183 of the inner member 185 is chamfered to a sharp edge 187 for cutting. The inner member 185 simultaneously rotates about its axis and translates along its axis to cut tissue. The cutting surface of the distal end 183 of the inner member 185 shears the tissue. For example, referring to FIG. 10, the cutting device 100 is placed tangentially against the targeted tissue such that the cutting window 170 exposes the inner member 185 to the tissue. As the inner member 185 rotates and translates, as shown by the arrows, the tissue within the cutting window catches on the hook 174 to initiate the cut and then the cutting edge 183 of the inner member 185 shears the tissue as the inner member 185 advances to cut the tissue. The cut is completed as the cutting edge 183 of the inner member 185 advances beyond the hook 174 of the cutting window 170 within the outer member 186.

FIG. 11 shows an alternative implementation of the inner member. The distal end 283 of the inner member 285 may be angled to a chamfered point so that the cut in the targeted tissue is initiated on one side and then extends across the width of the tissue. Similarly, when the cutting device is placed tangentially against the targeted tissue, the rotating and translating inner member 285 shears the tissue to be cut.

A number of implementations have been described. Nevertheless, it will be understood that various modifications may be made. For example, instead of a double helical channel, the helical member may include a single helical channel with a retractable follower and spring, or possibly, attraction and repelling forces of magnets or a solenoid could enable the rotating and reciprocating movements. Also, alternatively, the inner and outer members may have a cross-sectional shape other than circular. Additionally, the shape of the hook of the outer member may be modified in order to improve grasping of the tissue or grasping a larger volume of tissue. Accordingly, other implementations are within the scope of the following claims.

What is claimed is:

1. A surgical instrument, comprising:
   a cutting member including an implement for cutting tissue; and
   a drive coupled to the cutting member to simultaneously rotate, translate, and reciprocate the cutting member in response to only a rotational force applied to the drive in a single direction and to cut tissue during simultaneous rotation and translation of the cutting member, wherein the drive includes a drive member having a helical groove, and wherein the cutting member rotates about a longitudinal axis and translates along the longitudinal axis.

2. The surgical instrument of claim 1, wherein drive member is coupled to the cutting member.

3. The surgical instrument of claim 2, wherein the drive further includes a translation piece.

4. The surgical instrument of claim 3, wherein the translation piece is disposed in the helical groove of the drive member such that rotation of the drive member causes the cutting member to translate.

5. The surgical instrument of claim 1, wherein the helical groove makes at least two revolutions around the drive member and is configured to cause the cutting member to translate in a first direction, directly from a first location to a second location, along an axis of the cutting member while the drive member completes at least two full rotations.

6. The surgical instrument of claim 1, wherein the helical groove comprises a left-hand threaded helical channel and a right-hand threaded helical channel.

7. The surgical instrument of claim 6, wherein the left-hand threaded helical channel and the right-hand threaded helical channel blend together at their ends to form a continuous groove such that there is a smooth transition from the left-hand threaded helical channel to the right-hand threaded helical channel.

8. The surgical instrument of claim 7, wherein the cutting member is received within an outer tubular member, the outer tubular member including a cutting window disposed proximate to a tip of the outer tubular member.

9. The surgical instrument of claim 8, wherein the cutting window includes an opening in the outer tubular member exposing the cutting member to tissue.

10. The surgical instrument of claim 9, wherein the right-hand threaded helical channel, the left-hand threaded helical channel, or both make two complete revolutions around the drive member and is configured to cause the cutting member to translate in a first direction, directly from a first location to a second location, along an axis of the cutting member while the drive member completes at least two full rotations.

11. The surgical instrument of claim 9, wherein translation of the cutting member over a complete translational path of the cutting member requires the cutting member to complete more than one full rotation.

12. A surgical instrument, comprising:
   a cutting member including an implement for cutting tissue; and
   a drive coupled to the cutting member to simultaneously rotate, translate, and reciprocate the cutting member in response to only a rotational force applied to the drive in a single direction and to cut tissue during simultaneous rotation and translation of the cutting member, the drive including a drive member having a helical groove, the helical groove of the drive member including a left-hand threaded helical channel and a right-hand threaded helical channel, the left-hand threaded helical channel and the right-hand threaded helical channel being blended together at both ends to form a continuous groove, and the left-hand threaded helical channel, the right-hand threaded helical channel, or both making at least two revolutions around the drive member between the blended ends, wherein the cutting member rotates about a longitudinal axis and translates along the longitudinal axis.

13. A surgical instrument, comprising:
- a cutting member including an implement for cutting tissue;
- a drive coupled to the cutting member to simultaneously rotate, translate, and reciprocate the cutting member in response to only a rotational force applied to the drive in a single direction and to cut tissue during simultaneous rotation and translation of the cutting member, the drive including a drive member having a helical groove extending at least two revolutions around the drive member; and
- an outer tubular member, the cutting member being received within the outer tubular member, the outer tubular member including a cutting window disposed proximate to a tip of the outer tubular member.

14. The surgical instrument of claim 13, wherein the cutting member rotates about a longitudinal axis and translates along the longitudinal axis.

\* \* \* \* \*